(12) United States Patent
Schall et al.

(10) Patent No.: US 6,231,618 B1
(45) Date of Patent: *May 15, 2001

(54) PROSTHETIC LIMB INCLUDING AN ADJUSTABLE PYRAMIDAL LINK PLATE ASSEMBLY

(75) Inventors: Scott Schall, Englewood; Tracy Slemker; Lanny Wiggins, both of Miamisburg; Steven Steinbarger, Wilmington, all of OH (US)

(73) Assignees: Prosthetic Design, Inc., Clayton; CaTech, Inc., Centerville, both of OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,003

(22) Filed: Aug. 19, 1999

Related U.S. Application Data

(63) Continuation of application No. 09/042,371, filed on Mar. 13, 1998, now Pat. No. 6,033,440.
(60) Provisional application No. 60/040,421, filed on Mar. 13, 1997.

(51) Int. Cl.$^7$ ........................................................ A61F 2/62

(52) U.S. Cl. .................................. 623/38; 623/33; 623/53

(58) Field of Search ................................ 623/38, 33, 39, 623/47, 53, 27

(56) References Cited

U.S. PATENT DOCUMENTS

| 3,659,294 | 5/1972 | Glabiszewski . |
| 4,007,496 | 2/1977 | Glabiszewski . |
| 4,536,898 | 8/1985 | Palfray . |
| 4,608,054 | 8/1986 | Schröder . |
| 4,795,474 | 1/1989 | Horvath . |

(List continued on next page.)

FOREIGN PATENT DOCUMENTS

| 638095 | 9/1980 | (CH) . |
| 3937379 | 5/1991 | (DE) . |
| 610124 | 1/1994 | (EP) . |
| 2410998 | 12/1977 | (FR) . |
| 2630641 | 5/1988 | (FR) . |
| 1208421 | 10/1970 | (GB) . |
| 8089519 | 4/1996 | (JP) . |

(List continued on next page.)

Primary Examiner—Bruce Snow
(74) Attorney, Agent, or Firm—Thompson Hine & Flory LLP

(57) ABSTRACT

A pyramidal link-plate assembly for coupling a prosthetic limb upright assembly to another prosthetic limb component includes: a base plate member having a dome extending from a distal end and a cavity opening onto a distal apex of the dome, where the cavity includes a conically shaped portion with a diameter that widens with the distance from the distal apex of the dome; and a rotatable member which includes a substantially conically shaped body positioned within the conical portion of the cavity and which includes a frustopyramidal boss extending distally therefrom out through the opening in the distal apex of the dome. The conically shaped body of the rotatable member, positioned within the cavity, also widens with the distance from the distal apex of the dome. The boss is adapted to be received within an a central opening of a conventional annular coupling-socket. Set screws that extend radially into the central opening of the coupling socket are angled slightly distally so that when the set screws abut the outwardly angled faces of the frustopyramidal boss, further tightening of the set screws acts to pull the boss component in the distal direction, thereby causing the outer conical surface of the rotatable member's conically shaped body to press against the inner conical surface of the cavity. Accordingly, when the set screws are tightened, surface friction between the two complimentary conical surfaces prohibits further rotation of the rotatable member within the base plate member.

8 Claims, 7 Drawing Sheets

U.S. PATENT DOCUMENTS

| | | |
|---|---|---|
| 4,938,775 | 7/1990 | Morgan . |
| 4,969,911 | 11/1990 | Greene . |
| 5,047,063 | 9/1991 | Chen . |
| 5,163,965 | 11/1992 | Rasmusson et al. . |
| 5,376,129 | 12/1994 | Faulkner et al. . |
| 5,425,782 | 6/1995 | Phillips . |
| 5,443,526 | 8/1995 | Hoerner . |
| 5,458,657 | 10/1995 | Rasmusson . |
| 5,482,513 | 1/1996 | Wilson . |
| 5,507,837 | 4/1996 | Laghi . |
| 5,529,576 | 6/1996 | Lundt et al. . |
| 5,545,230 | 8/1996 | Kinsinger et al. . |
| 5,549,710 | 8/1996 | Vera et al. . |
| 5,759,206 | 6/1998 | Bassett . |
| 6,013,105 * | 1/2000 | Potts ................... 623/38 |
| 6,033,440 * | 3/2000 | Schall et al. ................... 623/38 |

FOREIGN PATENT DOCUMENTS

| | | |
|---|---|---|
| 8294504 | 11/1996 | (JP) . |
| 1109152 | 8/1984 | (RU) . |
| 1217404 | 3/1985 | (RU) . |
| 1553115 | 3/1990 | (RU) . |

* cited by examiner

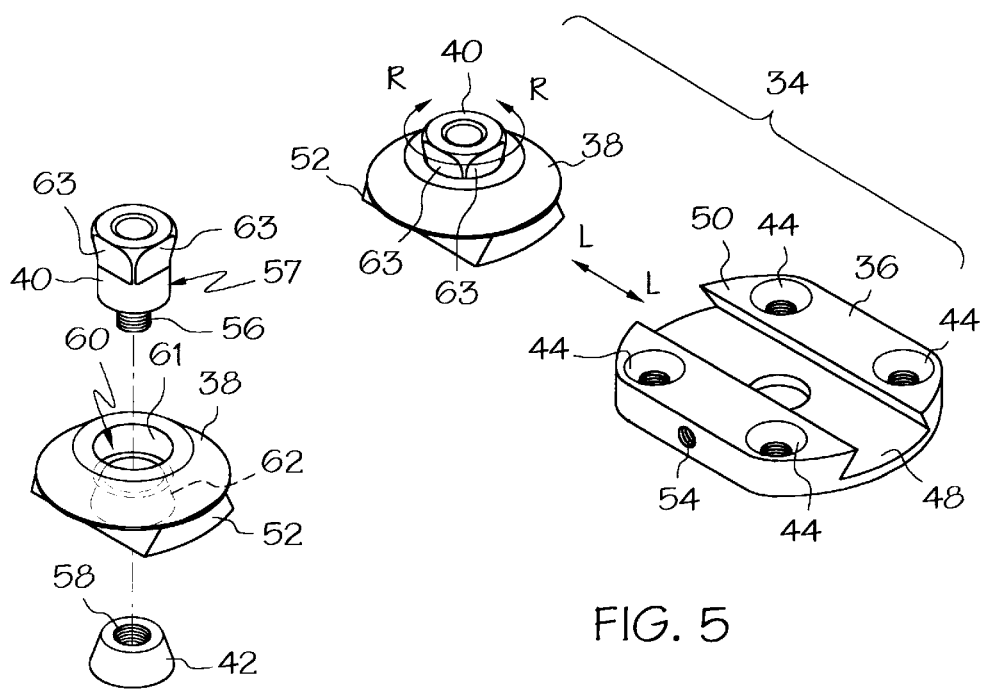
FIG. 4
FIG. 5
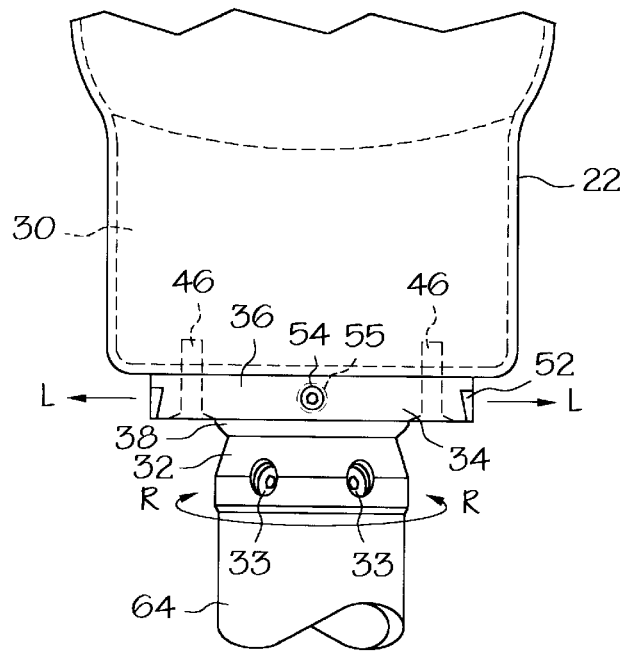
FIG. 6

PROSTHETIC LIMB INCLUDING AN ADJUSTABLE PYRAMIDAL LINK PLATE ASSEMBLY

CROSS REFERENCE TO RELATED APPLICATIONS

This Application is a Continuation Application of Ser. No. 09/042,371, filed Mar. 13, 1998 now U.S. Pat. No. 6,033,440.

The present application claims priority under 35 U.S.C. §119 from U.S. Provisional Patent Application, Ser. No. 60/040,421, filed Mar. 13, 1997; the disclosure of which is incorporated herein by reference, in its entirety.

BACKGROUND

The present invention relates to prosthetic devices, and more particularly, to a prosthetic limb pyramidal link-plate assembly which provides for infinite rotational adjustments.

As shown in FIG. 1a, a conventional pyramidal link-plate 10 will have a frustopyramidal, four-sided boss 12 projecting from a dome-shaped, or a spherically convex base 14, which in turn projects from a plate member 16. The plate member 16 will typically include four screw or bolt-receiving, through-holes 18 corresponding to a standard (within the industry) four-hole pattern. The conventional pyramidal link-plate 10 is primarily based upon the "Adjustable Link" described in U.S. Pat. No. 3,659,294 to Glabiszewski, the disclosure of which is incorporated herein by reference.

As shown in FIG. 1b, a prosthetic limb 20 for a transfemoral amputee will include a prosthetic limb socket 22 for receiving the wearer's residual limb, a knee joint assembly 24, a first pylon component 23 between the prosthetic limb socket and the knee joint assembly, interconnection components 26 for coupling the first pylon 23 to the prosthetic limb socket 22, interconnection components 27 for coupling the first pylon to the knee joint assembly 24, an ankle/foot assembly 28, and a second pylon 29 coupled between the knee joint assembly 24 and the ankle/foot assembly 28. The interconnection components 26 may consists of a locking or suction assembly 30 (such as a Shuttle Lock component or a ProSeal component commercially available from Prosthetic Design, Inc.) positioned within a distal end of the prosthetic limb socket 22, the conventional pyramidal link-plate 10, and an annular coupling-socket adapter 32 for coupling the first pylon 23 to the distal boss 12 of the pyramidal link-plate 10. Likewise, the interconnection components 27 may consist of the conventional pyramidal link-plate 10 mounted to the knee-joint assembly and another annular coupling-socket adapter 32 for coupling the first pylon 23 to the distal boss 12 of the pyramidal link-plate 10. The plurality of set screws 33 extend radially and downwardly against the distal boss 12 of the pyramidal link-plate 10 and are tightened to securely mount the pyramidal link-plate 10 (and the respective prosthetic limb components fastened thereto) to the coupling-socket adapter 32 (and the first pylon 23).

In fitting prosthetic limbs to patients, it is often necessary for the prosthetist to modify the alignments and orientations of the various prosthetic limb components with respect to each other during the initial fitting or after the patient has worn the prosthetic limb for a period of time. The first pylon 23 is typically capable of being rotatably adjusted with respect the coupling-socket adaptors. However, with certain transfemoral amputees, the distance between the distal end of the patient's residual limb and the patient's natural knee center is very short; and if the combined length of the components between a prosthetic limb socket and the prosthetic knee joint is greater than the distance between the distal end of the patients residual limb and the patient's natural knee center, then the prosthetist may be forced to eliminate the first pylon 23. Otherwise the knee center on the prosthetic side will be too low, thus causing gate deviation.

When the first pylon 23 is eliminated, the means to rotatably adjust the various prosthetic limb components is also lost. Accordingly, there are existing pyramidal link-plate components which offer sliding and/or rotating capabilities to such components. The disadvantage with the conventional sliding and/or rotating pyramidal link-plate components is that to provide such adjustability, the profile and/or the length of the component must be increased. Other rotatably adjustable pyramidal link-plate components only allow finite or incremental rotation and are difficult to adjust.

For example, one known rotatably adjustable pyramidal link-plate assembly includes a dome shaped component having the pyramidal boss extending from its apex, where the dome shaped component includes an upwardly facing (i.e., facing in towards the apex of the dome), serrated, annular ring positioned around an outer circumference of the base of the dome. The assembly also includes a planar base plate component having four screw-holes extending therethrough arranged in a standard four-hole pattern. The planar base plate also has a central hole, sized for receiving the dome portion of the dome shaped component therethrough. On the underside of the planar base plate, encircling the central hole, is a serrated, annular ring adapted to engage with the upwardly facing serrated, annular ring of the dome shaped component when the dome shaped component is inserted through the underside of the central hole. When the two components are assembled, and installed onto a prosthetic limb component by tightening four screws extending through the screw-holes, the two components are rotationally locked with respect to each other. To rotatably adjust the two components with respect to each other, the four screws must be loosened enough to allow the base plate component to be lifted from the dome shaped component to a sufficient extent so that the two serrated rings disengage from one another. Once the rotational adjustment is made, the screws are tightened again.

One disadvantage with this design is that the serrations, or teeth, allow for only finite (e.g. 5 or 6 degree increments) rotational adjustments. Additionally, it is often-times difficult to have access to the four screws extending through the base plate component (especially when the prosthetic limb socket and knee joint assembly are positioned in close proximity to one another). To access the four screws in such a situation, the adjustable pyramid link-plate assembly must first be separated from the female coupling-socket adapter. Accordingly the prosthetist will essentially have to disassemble the prosthetic limb to adjust rotational alignment.

Accordingly, there is a need for a prosthetic limb pyramidal link-plate component that provides rotatable adjustment to the prosthetic limb, yet does not significantly increase the profile or length of the attachment of the interconnection components; there is a need for a prosthetic limb pyramidal link-plate component that provides for infinite rotational adjustments; and there is a need for a prosthetic limb pyramidal link-plate component that does not require disassembly of the various interconnection components to allow for rotational adjustments.

SUMMARY

The present invention is a rotatably adjustable pyramidal link-plate assembly which does not require the prosthetic limb to be removed or disassembled prior to adjustment, and which provides for infinite rotatable adjustments without substantially increasing the profile and/or length of the conventional pyramidal link-plate components. In one embodiment, the present invention also provides a dimension of lateral adjustment without requiring the prosthetic limb to be removed or disassembled prior to adjustment and without significantly increasing the profile and/or length of the component.

The present invention provides a pyramidal link-plate assembly for coupling a prosthetic limb upright assembly to another prosthetic limb component. The pyramidal link-plate assembly present invention comprises a base plate member, which includes a dome extending from a distal end and a cavity opening onto a distal apex of the dome, where the cavity includes an inner circumferential surface with a diameter that widens with the distance from the distal apex of the dome. The pyramidal link-plate assembly also comprises a rotatable member which includes a first portion positioned within the cavity, where the first portion has a complimentary outer circumferential surface with a diameter that widens with the distance from the distal apex of the dome, and the rotatable member also includes a frustopyramidal boss portion extending distally therefrom out through the opening in the distal apex of the dome. Finally, the pyramidal link-plate assembly comprises a means for securely mounting the base plate member to a prosthetic limb component. The boss portion is adapted to be received within an a central opening of a conventional annular coupling-socket mounted to the proximal end of an upright assembly.

The annular coupling-socket includes a plurality of set screws extending radially into the central opening of the coupling-socket, which are angled slightly distally. The set screws abut the outwardly angled faces of the frustopyramidal boss portion extending into the opening such that when the set screws are tightened the rotatable member is pulled in the distal direction, thereby causing the outer circumferential surface of the first portion of the rotatable member to press against the inner circumferential surface of the cavity. Accordingly, when the set screws are tightened, surface friction between the two complimentary circumferential surfaces causes rotation of the rotatable member within the base plate member is inhibited. Preferably, the outer circumferential surface of the first portion of the rotatable member and the inner circumferential surface of the cavity are both relatively smooth, so as to allow for infinite rotational adjustments of the rotatable member with respect to the base-plate member.

Thus, for the prosthetist to rotatably adjust the upright assembly with respect to the prosthetic limb component, only a pair of adjacent set screws in the coupling-socket need to be loosened to allow rotation of the rotatable member with respect to the base plate. Once the prosthesis rotatably adjusts the upright assembly to the desired rotation, the set screws are tightened again to inhibit rotation of the rotatable member with respect to the base plate member. Therefore, the invention allows for infinite rotational adjustment of the pyramidal link-plate without requiring the disassembly of the prosthetic limb components.

In another embodiment of the present invention the base plate member include a proximal plate and a distal plate stacked upon each other, where the proximal plate includes a dove-tail shaped tooth extending from a distal surface thereof and the distal plate includes a complementary dove-tail shaped groove extending into its proximal end and receiving the dove-tail shaped tooth therein. The dove-tail shaped groove is laterally longer than a dove-tail shaped tooth, therefore the dove-tail shaped tooth is laterally slidable within the dove-tail shape groove. The base plate member further includes a mechanical lock to inhibit lateral sliding of the distal plate with respect to the proximal plate.

Thus, for the prosthetist to laterally adjust the upright assembly with respect to the prosthetic limb component, the prosthetist will first loosen the mechanical lock to allow lateral sliding of the proximal plate with respect to the distal plate. Next, the prosthetist will laterally adjust the prosthetic limb component with respect to the upright assembly. Once the proper alignment is achieved, the prosthetist will tighten the mechanical lock again so as to inhibit further lateral movement of the two components with respect to each other.

Accordingly, it is an object of the present invention to provide a pyramid link-plate component which facilitates rotatable adjustment without significantly increasing the profile and/or length of the component, which is easily manufactured, which is light weight and low costs. It is an object of the present invention to provide a pyramid link-plate component that provides infinite rotational adjustments. It is an object of the present invention to provide a pyramid link-plate component in which rotational adjustment is facilitated upon the loosening of easily accessible, set screws. It is also an object of the present invention to provide the rotatably adjustable pyramid link-plate component which is also laterally adjustable at least in one direction.

It is a further object of the present invention to provide a link plate assembly that includes: a base plate member having a dome extending from a distal end of the base plate member and a cavity opening onto a distal apex of the dome, where the cavity has an inner circumferential surface with a diameter that widens with the distance from the distal apex of the dome; and a rotatable member having a first portion positioned within the cavity, where the first portion has an outer circumferential surface with a diameter that widens with the distance from the distal apex of the dome, and where the rotatable member also has a frustopyramidal boss portion extending distally through the opening in the distal apex of the dome. Therefore, when distal pressure is applied to the outwardly angled faces of the frustopyramidal boss portion, the rotatable member is pulled in the distal direction, causing the outer circumferential surface of the first portion of the rotatable member to press against the inner circumferential surface of the cavity, thereby substantially prohibiting further rotation of the rotatable member with respect to the base plate member.

It is a further object of the present invention to provide a link plate assembly that includes: a base plate member having a dome extending from a distal end of the base plate member and a cavity opening onto a distal apex of the dome; and a rotatable member having a first portion positioned within the cavity, where the rotatable member also has a frustopyramidal boss portion extending distally through the opening in the distal apex of the dome; wherein, when distal pressure is applied to the outwardly angled faces of the frustopyramidal boss portion, the rotatable member is pulled in the distal direction, causing an outer surface of the first portion of the rotatable member to press against an inner surface of the cavity, thereby substantially prohibiting further rotation of the rotatable member with respect to the base plate member.

Other objects and advantages of the present invention will be apparent from the following description, the accompanying drawings and the appended claims.

BRIEF DESCRIPTION OF THE DRAWINGS

FIG. 4 is an exploded, perspective view of a sliding proximal plate component of the first embodiment of the pyramidal link-plate assembly;

FIG. 5 is a perspective, exploded view of the first embodiment of the pyramidal link-plate assembly;

FIG. 6 is a perspective view of a prosthetic limb assembly incorporating the first embodiment of the pyramidal link-plate assembly;

DETAILED DESCRIPTION

Figure 1A:
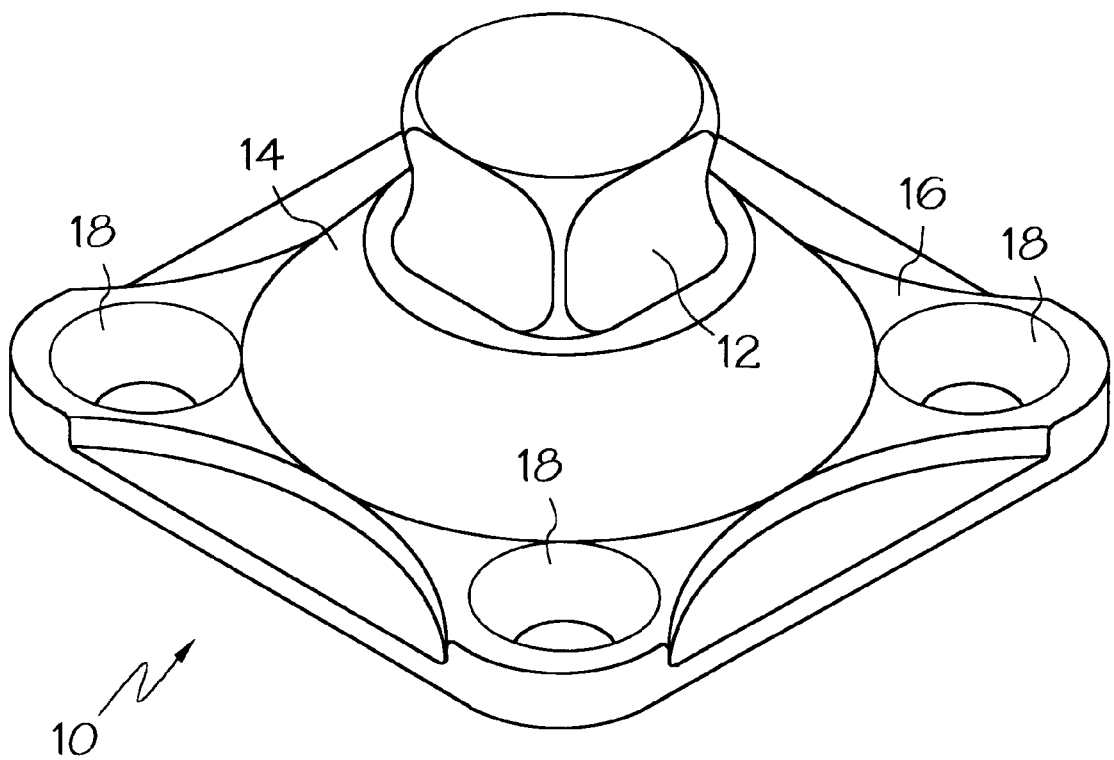
FIG. 1a is a perspective view of a prior-art pyramidal link-plate (described above)

The preferred embodiments of the present invention are described and illustrated below as adjustably coupling a prosthetic limb socket to a prosthetic limb upright assembly. The various orientational or positional terms (i.e., "distal" or "proximal") used to describe the elements of the inventions are therefore used according to this frame of reference. Of course, it will be apparent to those of ordinary skill in the art that the present inventions may also be used to adjustably couple, for example, a prosthetic foot component to a prosthetic limb upright assembly. In this alternate frame of reference, the orientations or positions of the elements of the inventions would be different. However, for the purpose of clarity, in describing and claiming the inventions, only the first frame of reference will be used; and it will therefore be understood that the positional and orientational terms used to describe the elements of the invention are only used to describe the elements in relation to each other. For example, when the present invention is used to adjustably couple a prosthetic foot component to a prosthetic limb upright assembly, those elements of the present invention indicated in the following disclosure as being "distal" will actually be "proximate" elements, and vice versa As shown in FIGS. 2–6, a first embodiment of the present invention provides an adjustable pyramidal link-plate assembly 34 which is both rotatably adjustable and laterally adjustable. The adjustable pyramidal link-plate assembly 34 includes a proximal attachment-plate component 36; a distal, spherically convex or dome-shaped base-plate component 38 stacked upon and laterally slidable with respect to the attachment-plate component 36; a frustopyramidal boss component 40; and a frustoconical boss attachment component 42. The attachment-plate component 36 includes a plurality of screw holes 44 extending therethrough which are preferably in a conventional four-hole pattern (such as the European four-hole pattern) as is known to those of ordinary skill in the art. The screw holes 44 are provided so that screws 46 (see FIG. 6) may be threaded therein so as to secure the attachment-plate component 36 to a distal end of a prosthetic limb socket 22 or to any other prosthetic limb component such as a prosthetic limb foot component or a prosthetic joint component. It will be apparent to those of ordinary skill in the art that there are many means for securing the attachment-plate component 36 to a prosthetic limb component. Such means may include applying adhesives between the components, molding the components together, forming the components as a unitary component, using other arrangements of bolts/screws, etc.; all of which are within the scope of the present invention.

The attachment-plate component 36 also includes a dovetail shaped groove 48 extending into a distal surface 50 of the plate, and extending diametrically across the distal surface 50 of the plate. The dome-shaped base-plate component 38 has a complimentary, dove-tail shaped tooth 52 extending proximally therefrom and shaped to be received and slide laterally within the groove 48 of the attachment-plate component 36. The attachment-plate component 36 also includes a set screw 54 extending partially into a radially extending, partially threaded channel 55. The set screw abuts a plug 59 having a forward edge shaped to contact a side surface of the dove-tail shaped tooth 52. Tightening of the set screw 54 forces the plug 59 against the side surface of the dove-tail shaped tooth 52. The set screw 54 and plug 59 are therefore used as a releasable mechanical lock to secure the base-plate component 38 and the attachment-plate component 36 in a fixed lateral position with respect to each other when the set screw 54 is tightened. When the set screw 54 is loosened, the plug 59 may reciprocate back into the channel 55, allowing the dove-tail shaped tooth 52 to laterally slide again within the dove-tail shaped groove 48.

The frustopyramidal boss component 40 and the frustoconical boss-attachment component 42 are adapted to engage with, and lock to each other by means of a male fastener projection 56 extending from the boss component 40 and a female fastener receptacle 58 extending into the boss-attachment component 42. The boss component 40 and the boss-attachment component 42 are adapted to mate with each other and lock to each other within a cavity 60 extending axially through the dome-shaped base-plate component 38. The cavity 60 has a conical portion 62 shaped to receive the boss-attachment component 42. The cavity also includes a cylindrical portion 61, opening onto the distal apex of the dome, that is adapted to receive a complimentary-shaped cylindrical portion 57 of the boss component 40. The complimentary shapes of the cavity 60 and of the boss and boss-attachment components 40, 42 allow for the boss and boss-attachment components 40, 42 to rotate within the base-plate component 38 as shown by arrows R—R.

Figure 3:
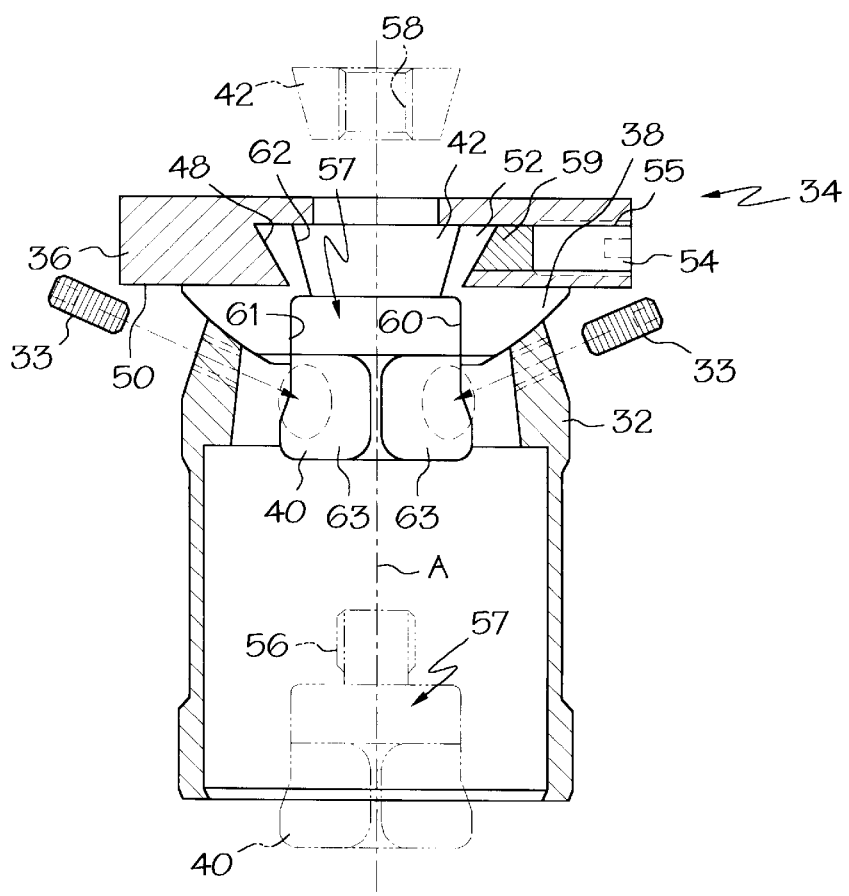
FIG. 3 is an elevational, cross-sectional view of the first embodiment of the pyramidal link-plate assembly, showing an exploded view of frustopyramidal boss component and the frustoconical boss attachment components in phantom, coupled to a conventional, annular coupling-socket.

As shown in FIG. 3, when the adjustable pyramidal link-plate assembly 34 is coupled to an annular coupling-socket adapter 32 the plurality of set screws 33 are used to securely mount the adjustable pyramidal link-plate assembly 34 (and the prosthetic limb components fastened thereto) to the coupling-socket adapter 32 (and the prosthetic limb components fastened thereto). The vertical faces 63 of the frustopyramidal boss component 40 are angled slightly outwardly with respect to the vertical axis A, and the radially extending set screws 33 are angled slightly distally so as to abut flush against the outwardly angled faces 63 of the boss component 40 when tightened thereagainst. Accordingly, the tightening of the set screws 33 against the corresponding faces 63 of the boss component acts to push the boss component 40 in the axial direction, and in turn, acts to press the outer conical surface of the frustoconical boss-attachment component 42 against the inner conical surface of the conical portion 62 of the cavity 60. Accordingly, surface friction between the two abutting conical surfaces prohibits further rotation of the components with respect to each other. Because the outer conical surface of the frustoconical boss-attachment component 42 and opposing the inner conical surface of the conical portion 62 of the cavity 60 are preferably both substantially smooth (i.e., there are no engaging grooves/projections or engaging serrations), infinite rotational adjustments of the components with respect to each other can be achieved. It is noted, however, that it is within the scope of the invention to provide engaging grooves and projections on the opposing conical surfaces if only incremental adjustments are desired.

Referring to FIG. 6, when the adjustable pyramidal link-plate assembly 34 used to couple a prosthetic limb upright assembly 64 (or any other prosthetic limb component such as a prosthetic limb knee joint) to a distal end of a prosthetic limb socket 22 (or to any other prosthetic limb component such as a prosthetic limb foot component) the upright 64 assembly is rotatably and laterally adjustable with respect to the socket 22 in the R—R and L—L directions. To rotatably adjust the upright assembly 64 with respect to the prosthetic limb socket 22, the set screws 33 will first be loosened, the necessary rotatable adjustments will be made, and then the set screws 33 will be tightened again. In practice, only an adjacent two of the set screws 33 need to be loosened to relieve the surface friction between the two conical surfaces, thus allowing for rotational adjustment to be achieved. To laterally adjust the upright assembly 64 with respect to the prosthetic limb socket 22 the set screw 54 will first be loosened, the necessary lateral adjustment will be made, and then the set screw 54 will be tightened again.

Figure 7:
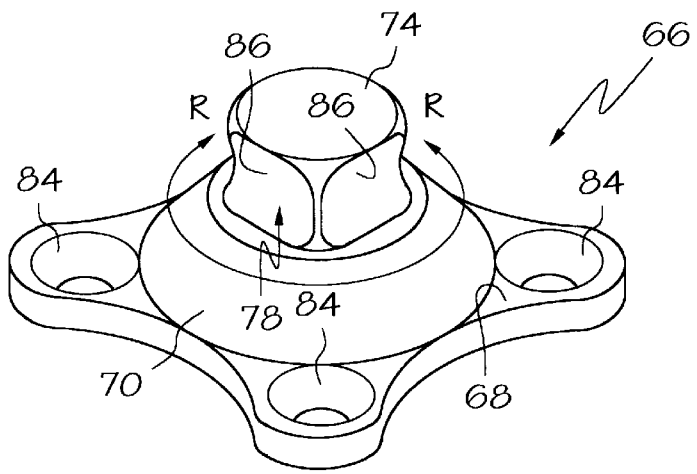
FIG. 7 is a perspective view of a second embodiment of a pyramidal link-plate assembly of the present invention.
Figure 8:
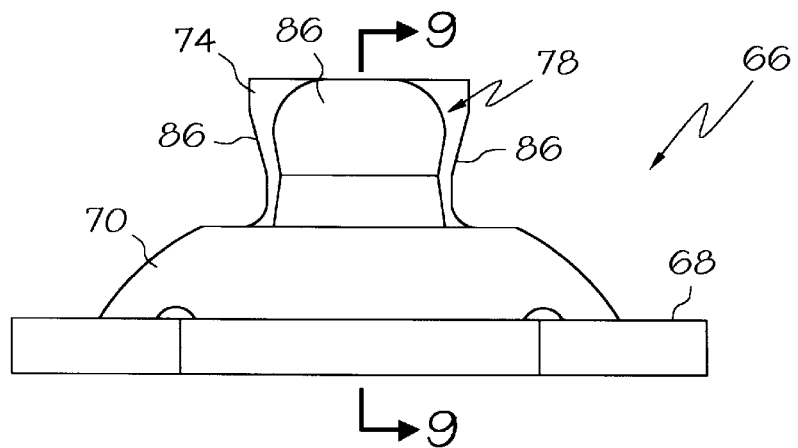
FIG. 8 is an elevational view of the second embodiment of the pyramidal link-plate assembly.
Figure 9:
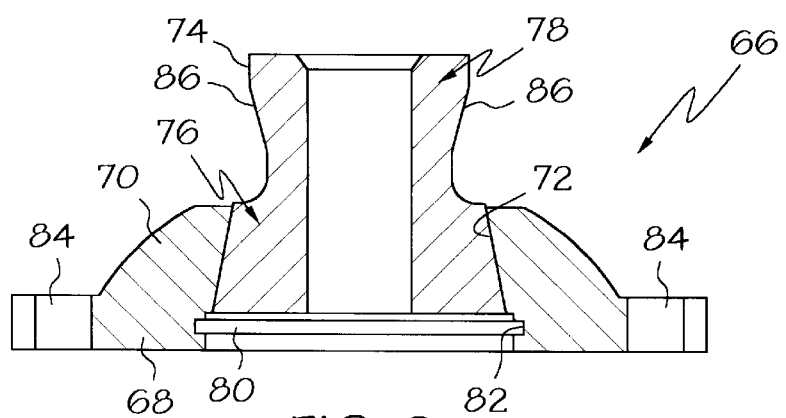
FIG. 9 is a cross sectional view taken along lines FIG. 9—9 of FIG. 8.

As shown in FIGS. 7–9, a second embodiment of the present invention provides an adjustable pyramidal link-plate assembly 66 which is only rotatably adjustable. The adjustable pyramidal link-plate assembly 66 includes a base-plate member 68 having a dome 70 extending from a distal end of the base-plate member and a substantially conical cavity 72 opening onto a distal apex of the dome, where the cavity 72 widens with the axial distance from the distal apex of the dome. The base-plate member 68 is preferably machined from a metallic material such as aluminum; however, other suitable materials may be used depending upon the application.

The adjustable pyramidal link-plate assembly 66 also includes a rotatable member 74 having a substantially conically shaped portion 76 rotatably received within the conical cavity 72. The rotatable member 74 also includes a frustopyramidal boss portion 78 ending distally therefrom and out through the opening in the distal apex of the dome. The rotatable member 74 is preferably machined from a titanium-based metallic material; however, other suitable materials and/or metals may be used depending upon the application.

The adjustable pyramidal link-plate assembly 66 also includes a metallic retainer ring 80 for retaining the rotatable member 74 within the cavity 72. The retainer ring 80 is preferably made of spring metal so that it can be flexed to be received within a correspondingly shaped annular groove 82 positioned within a proximal end of the cavity 72.

The adjustable pyramidal link-plate assembly 66 finally includes a plurality of through holes 84 preferably arranged in a standard four-hole pattern and adapted to securely mount the adjustable pyramidal link-plate assembly 66 to another prosthetic limb component, such as a prosthetic limb socket component. The complimentary shapes of the cavity 72 and of the conically shaped portion 76 of the rotatable member 74 allow for the rotatable member 74 to rotate within the base-plate member 68 as shown by arrows R—R.

Figure 10:
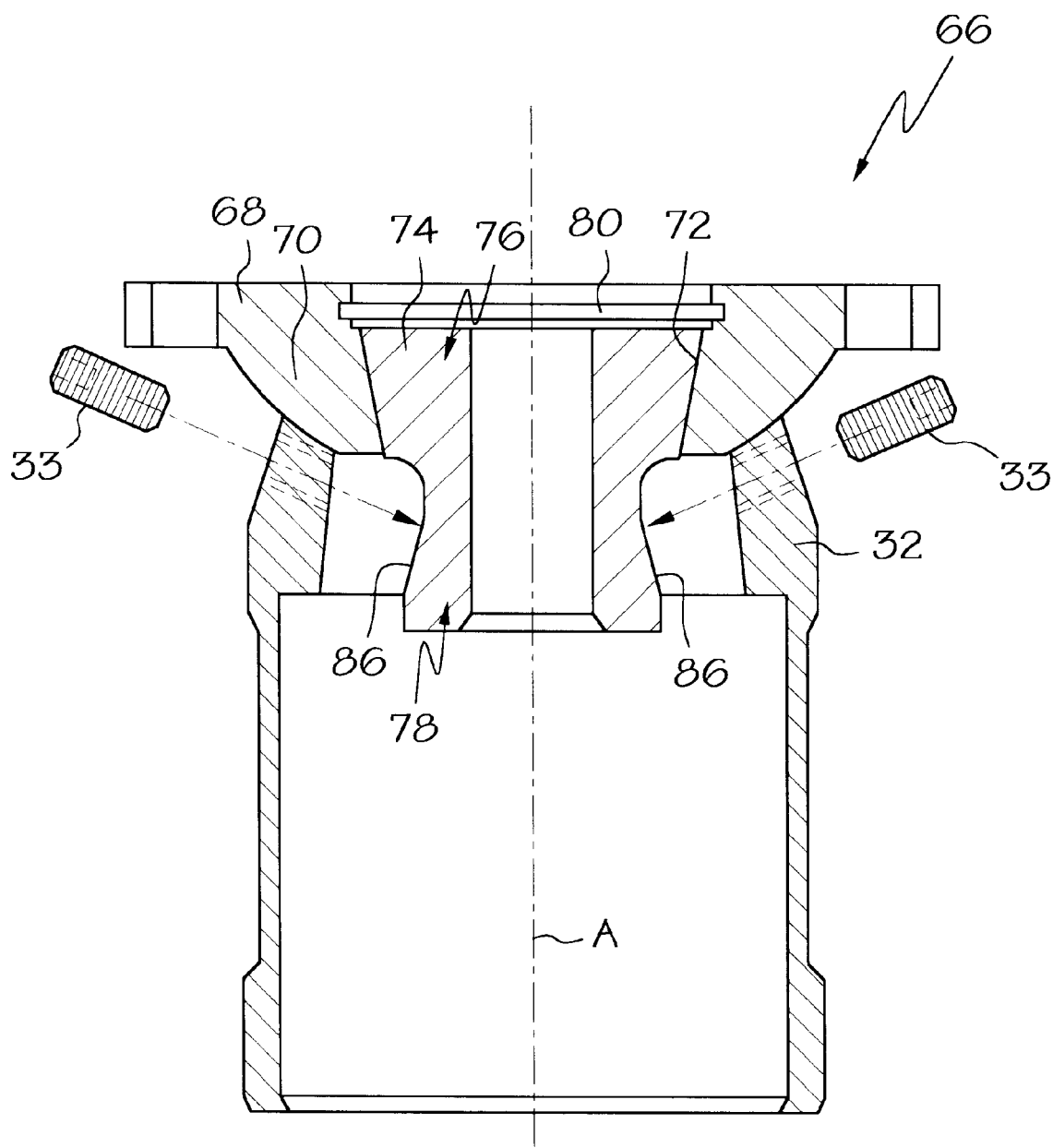
FIG. 10 is an elevational, cross-sectional view of the second embodiment of the pyramidal link-plate assembly coupled to a conventional, annular coupling-socket.

As shown in FIG. 10, the adjustable pyramidal link-plate assembly 66 operates in a similar fashion as the first embodiment of the present invention described above. When the adjustable pyramidal link-plate assembly 66 is coupled to an annular coupling-socket adapter 32 the plurality of set screws 33 are used to securely mount the adjustable pyramidal link-plate assembly 66 (and any prosthetic limb components fastened thereto) to the coupling-socket adapter 32 (and any prosthetic limb components fastened thereto). The vertical faces 86 of the frustopyramidal boss portion 78 are angled slightly outwardly with respect to the vertical axis A, and the radially extending set screws 33 are angled slightly distally so as to abut flush against the outwardly angled faces 86 of the boss portion 78 when tightened thereagainst. Accordingly, the tightening of the set screws 33 against the corresponding faces 86 of the boss portion acts to push the rotatable member 74 in the axial direction, and in turn, acts to press the outer conical surface of the conical portion 76 against the inner conical surface of the cavity 72. The surface friction between the two abutting conical surfaces prohibits further rotation of the components with respect to each other. To rotatably adjust the two prosthetic limb components, coupled together by the adjustable pyramidal link-plate assembly 66, the set screws 33 will first be loosened, the necessary rotatable adjustments will be made, and then the set screws 33 will be tightened again. In practice, only an adjacent two of the set screws 33 need to be loosened to relieve the surface friction between the two conical surfaces, thus allowing for rotational adjustment to be achieved.

While the forms of apparatus herein described constitute preferred embodiments of this invention, it is to be understood that the invention is not limited to these precise forms of apparatus, and that changes may be made therein without departing from the scope of the invention.

For example, while the cavities and corresponding rotatable members are disclosed as being substantially conical, it is within the scope of the invention that the cavities and corresponding rotatable members be substantially hemispherical. It is also within the scope of the invention to provide an outer circumferential surface of the rotatable member that is adapted to abut against an inner, narrowing circumferential surface of a cavity within the base-plate member, where the outer circumferential surface may be an o-ring type member or any other suitable friction surface.

Additionally, while complimentary circumferential surfaces are preferred for the inner surface of the cavity and the outer surface of the rotatable member positioned within the cavity, it is within the scope of the invention to provide complimentary polygonal surfaces for these two elements. While sacrificing the infinite rotatable adjustability provided by the smooth, complementary circumferential surfaces, the complimentary polygonal surfaces will allow incremental rotational adjustments and will still provide a low overall profile and length for the link-plate assembly.

Figure 1B:
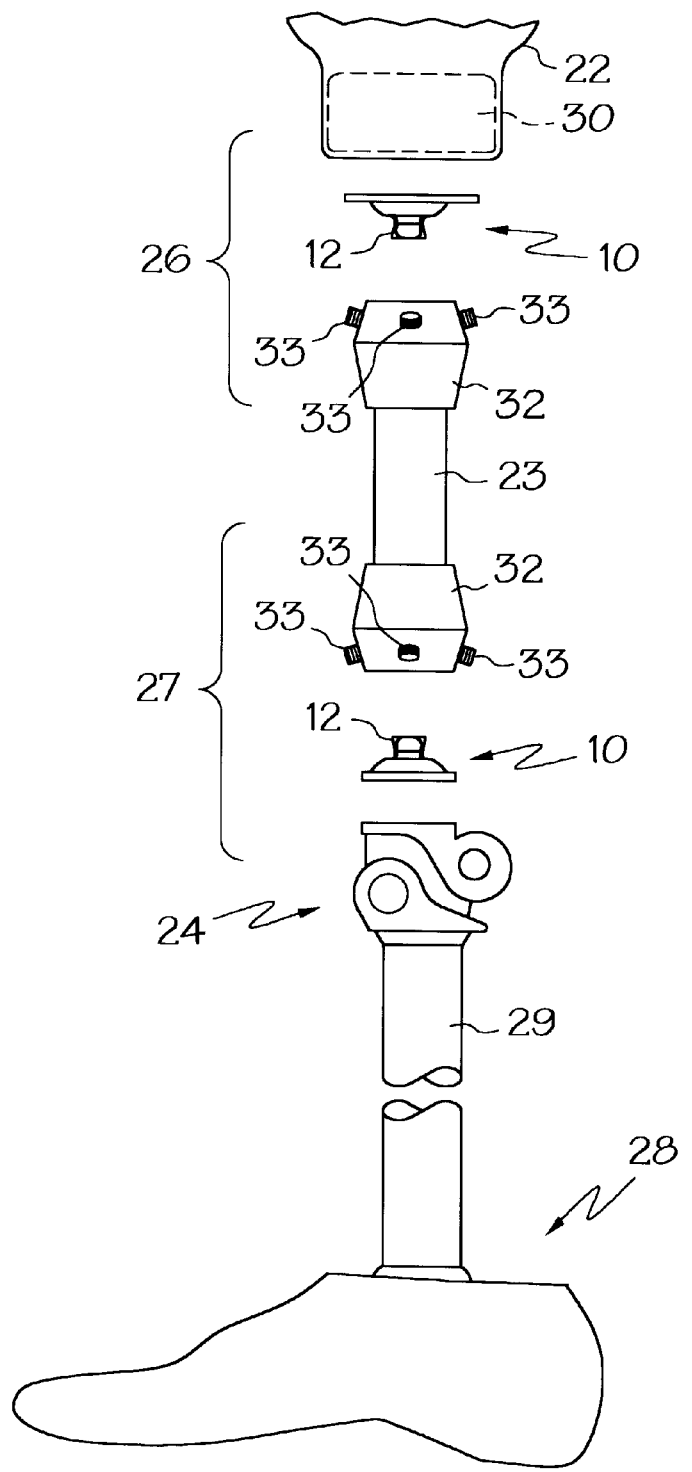
FIG. 1b is a perspective view of a prior-art prosthetic limb assembly utilizing the prior art pyramidal link-plate (described above)
Figure 2:
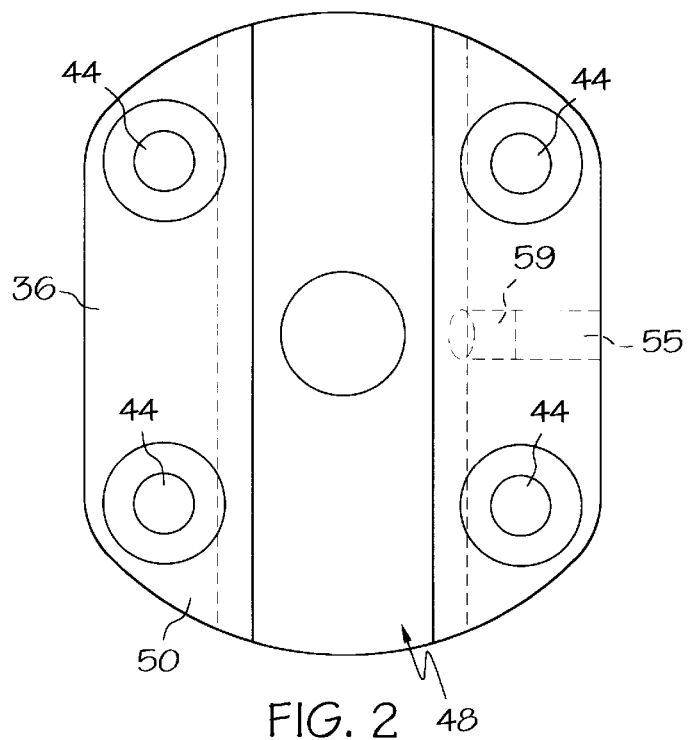
FIG. 2 is a top plan view of a distal plate component of a first embodiment of a pyramidal link-plate assembly of the present invention.
Figure 11:
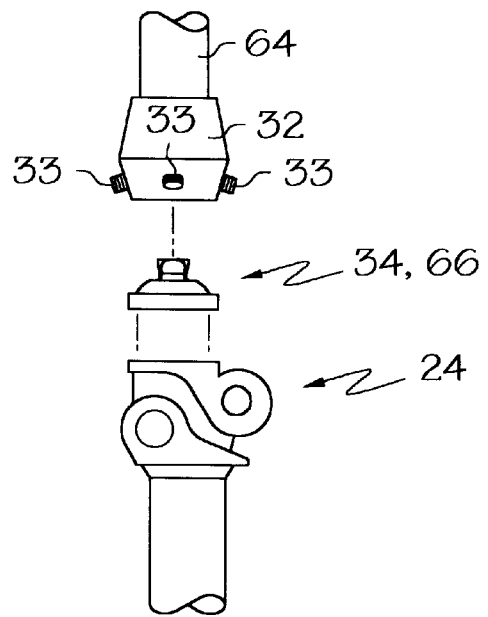
FIG. 11 is an elevational view of the pyramidal link-plate assembly of the present invention coupling a prosthetic knee-joint to another prosthetic limb component.
Figure 12:
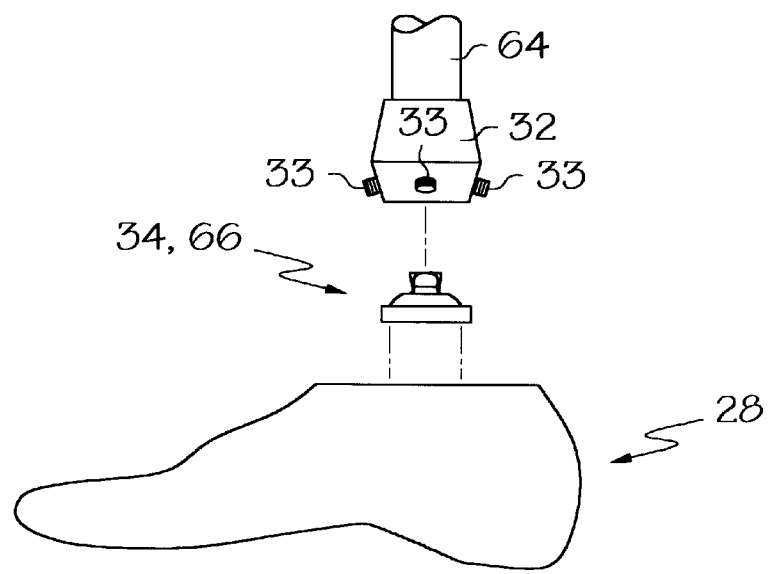
FIG. 12 is an elevational view of the pyramidal link-plate assembly of the present invention coupling a prosthetic foot to another prosthetic limb component.

Additionally, while the preferred embodiments described above depict the pyramidal link-plate assemblies 34/66 of the present invention useful for coupling a prosthetic limb upright assembly to a prosthetic limb socket 22, it is within the scope of the invention to utilize the link plate assemblies 34/66 of the present invention in any manner that conventional pyramidal link-plates 10 (See FIG. 1) have been used. For example, as shown in FIG. 11, it is within the scope to couple a prosthetic limb upright assembly 64 to a knee joint assembly 24 using a link plate assembly 34/66 of the present invention; and, as shown in FIG. 12, it is within the scope of the invention to couple a prosthetic limb upright assembly 64 to a prosthetic ankle/foot assembly 28.

What is claimed is:

1. A prosthetic limb, comprising:
   a first prosthetic limb component having an outer end surface;
   a second prosthetic limb component including a female coupling member extending therefrom, the female coupling member including a central bore;
   a link plate assembly coupling the second prosthetic limb component to the outer end surface of the first prosthetic limb component, the link plate assembly including,
      a base member having a cavity opening onto an end surface of the base member facing the second prosthetic limb component, the cavity having an inner circumferential surface with a diameter that widens with the distance from the end surface of the base member facing the second prosthetic limb component,
      a rotatable member, having a first portion positioned within the cavity, the first portion having an outer circumferential surface with a diameter that widens with the distance from the end of the base member facing the second prosthetic limb component, the rotatable member also having a boss portion extending out from the opening in the end of the base member facing the second prosthetic limb component and releasably secured in the central bore of the female coupling member, and
      a means for securely mounting base member of the link plate assembly to the outer distal end surface of the prosthetic limb socket component; and
      a threaded press forcing the outer circumferential surface of the first portion of the rotatable member to press against the inner circumferential surface of the cavity in the base member, thereby substantially inhibiting rotation of the rotatable member with respect to the base member;
   whereby rotatable adjustment of the second prosthetic limb component with respect to the first prosthetic limb component is performed by loosening the threaded press to allow rotation of the rotatable member with respect to the base member, rotating the second prosthetic limb component to the desired orientation, and then tightening the threaded press again.

2. The prosthetic limb of claim 1, wherein the first prosthetic limb component is a prosthetic limb socket component adapted to receive a patient's residual limb therein and the second prosthetic limb component is an upright assembly.

3. The prosthetic limb of claim 1, wherein the first prosthetic limb component is a prosthetic knee joint.

4. The prosthetic limb of claim 1, wherein the first prosthetic limb component is a prosthetic foot and the second prosthetic component is a prosthetic knee joint.

5. A prosthetic limb, comprising:
   a prosthetic limb socket component adapted to receive a patient's residual limb therein, the prosthetic limb socket component having an outer distal end surface;
   an upright assembly including an annular coupling adaptor extending proximally therefrom, the annular coupling adaptor including at least two diametrically opposed set screws extending radially into a central bore of the annular coupling adaptor, the set screws being angled distally; and
   a link plate assembly coupling the upright assembly to the outer distal end surface of the prosthetic limb socket component, the link plate assembly including,
      a base plate member having a dome extending from a distal end of the base plate member and a cavity opening onto a distal apex of the dome, the cavity having an inner circumferential surface with a diameter that widens with the distance from the distal apex of the dome,
      a rotatable member, having a first portion positioned within the cavity, the first portion having an outer circumferential surface with a diameter that widens with the distance from the distal apex of the dome, the rotatable member also having a boss portion extending distally through the opening in the distal apex of the dome, the boss portion having at least two opposing, outwardly angled, faces, and
      a means for securely mounting the base plate member to the outer distal end surface of the prosthetic limb socket component;
   the boss portion inserted within the central bore of the annular coupling adaptor and the set screws tightened against the opposing faces of the boss portion, causing the rotatable member to be pulled in the distal direction, and in turn causing the outer circumferential surface of the first portion of the rotatable member to abut and press directly against the inner circumferential surface of the cavity, thereby substantially inhibiting rotation of the rotatable member with respect to the base plate member;
   whereby rotatable adjustment of the upright assembly with respect to the prosthetic limb socket component is performed by loosening the set screws to allow rotation of the rotatable member with respect to the base plate, rotating the upright assembly to the desired orientation, and then tightening the set screws again.

6. A prosthetic limb, comprising:
   a prosthetic foot component having a proximal end;
   an upright assembly including an annular coupling adaptor extending distally therefrom, the annular coupling adaptor including at least two diametrically opposed set screws extending radially into a central bore of the annular coupling adaptor, the set screws being angled proximally; and
   a link plate assembly coupling the upright assembly to the distal end of the prosthetic foot component, the link plate assembly including,
      a base plate member having a dome extending from a proximal end of the base plate member and a cavity opening onto a proximal apex of the dome, the cavity having an inner circumferential surface with a diameter that widens with the distance from the proximal apex of the dome, a rotatable member, having a first portion positioned within the cavity, the first portion having an outer circumferential surface with a diameter that widens with the distance from the distal apex of the dome, the rotatable member also having a boss portion extending distally through the opening in the distal apex of the dome, the boss portion having at least two opposing, outwardly angled, faces, and a means for securely mounting the base plate member to the proximal end of the prosthetic foot component;

the boss portion inserted within the central bore of the annular coupling adaptor and the set screws tightened against the opposing faces of the boss portion, causing the rotatable member to be pulled in the proximal direction, and in turn causing the outer circumferential surface of the first portion of the rotatable member to press against the inner circumferential surface of the cavity, thereby substantially inhibiting rotation of the rotatable member with respect to the base plate member;

whereby rotatable adjustment of the upright assembly with respect to the prosthetic foot component is performed by loosening the set screws to allow rotation of the rotatable member with respect to the base plate, rotating the upright assembly to the desired orientation, and then tightening the set screws again.

7. A prosthetic limb, comprising:

a prosthetic joint component;

an upright assembly including an annular coupling adaptor extending therefrom, the annular coupling adaptor including at least two diametrically opposed set screws extending radially into a central bore of the annular coupling adaptor, the set screws being angled with respect to a central axis of the central bore; and a link plate assembly, positioned between the upright assembly and prosthetic joint component, coupling the upright assembly to the prosthetic joint component, the link plate assembly including, a base plate member having a dome extending from an end of the base plate member facing the upright assembly and a cavity opening onto an apex of the dome, the cavity having an inner circumferential surface with a diameter that widens with the distance from the apex of the dome, a rotatable member, having a first portion positioned within the cavity, the first portion having an outer circumferential surface with a diameter that widens with the distance from the apex of the dome, the rotatable member also having a boss portion extending out through the opening in the apex of the dome, the boss portion having at least two opposing, outwardly angled, faces, and a means for securely mounting the base plate member to the prosthetic joint component;

the boss portion inserted within the central bore of the annular coupling adaptor and the set screws being tightened against the opposing faces of the boss portion, causing the rotatable member to be pulled towards the upright assembly, and in turn causing the outer circumferential surface of the first portion of the rotatable member to press against the inner circumferential surface of the cavity, thereby substantially inhibiting rotation of the rotatable member with respect to the base plate member;

whereby rotatable adjustment of the upright assembly with respect to the prosthetic joint component is performed by loosening the set screws to allow rotation of the rotatable member with respect to the base plate, rotating the upright assembly to the desired orientation, and then tightening the set screws again.

8. A prosthetic limb, comprising:

a prosthetic limb socket component adapted to receive a patient's residual limb therein, the prosthetic limb socket component having an outer distal end surface;

an upright assembly including an annular coupling adaptor extending proximally therefrom, the annular coupling adaptor including at least two diametrically opposed set screws extending radially into a central bore of the annular socket, the set screws being angled distally; and a link plate assembly coupling the upright assembly to the outer distal end surface of the prosthetic limb socket component, the link plate assembly including, a base plate having a cavity opening onto a distal end surface of the base plate, the cavity having an inner circumferential surface with a diameter that widens with the distance from the distal end surface of the base plate, a rotatable link component, having a first portion positioned within the cavity, the first portion having an outer circumferential surface with a diameter that widens with the distance from the distal end surface of the base plate, the rotatable link component also having a boss portion extending distally through the opening in the distal end surface of the base plate, the boss portion having at least two opposing, outwardly angled, faces, and a means for securely mounting the base plate to the outer distal end surface of the prosthetic limb socket component;

the boss portion inserted within the central bore of the annular socket; and at least two threaded screws tightened so as to force the outer circumferential surface of the first portion of the rotatable link component to abut and press directly against the inner circumferential surface of the cavity, thereby substantially inhibiting rotation of the rotatable link component with respect to the base plate;

whereby rotatable adjustment of the upright assembly with respect to the prosthetic limb component is performed by loosening the threaded screws to allow rotation of the rotatable link component with respect to the base plate, rotating the upright assembly to the desired orientation, and then tightening the threaded screws again.

* * * * *

UNITED STATES PATENT AND TRADEMARK OFFICE
CERTIFICATE OF CORRECTION

PATENT NO.    : 6,231,618 B1
DATED         : May 15, 2001
INVENTOR(S)   : Scott Schall, et al.

It is certified that error appears in the above-identified patent and that said Letters Patent is hereby corrected as shown below:

Claim 4, column 10,
Line 5, after the word "prosthetic" (first occurrence), insert the word -- limb --.

Signed and Sealed this

Sixteenth Day of October, 2001

Attest:

*Attesting Officer*

NICHOLAS P. GODICI
*Acting Director of the United States Patent and Trademark Office*